United States Patent
Xia et al.

(10) Patent No.: US 10,155,113 B2
(45) Date of Patent: Dec. 18, 2018

(54) NEURAL PHYSIOLOGICAL APPARATUS FOR WAKEFULNESS

(71) Applicants: Qian Xia, Singapore (SG); Xiaoping Li, Singapore (SG)

(72) Inventors: Qian Xia, Singapore (SG); Xiaoping Li, Singapore (SG)

(*) Notice: Subject to any disclaimer, the term of this patent is extended or adjusted under 35 U.S.C. 154(b) by 0 days.

(21) Appl. No.: 14/335,910

(22) Filed: Jul. 20, 2014

(65) Prior Publication Data

US 2016/0220817 A1 Aug. 4, 2016

(51) Int. Cl.
| | |
|---|---|
| *A61N 1/36* | (2006.01) |
| *A61N 1/04* | (2006.01) |
| *A61B 5/16* | (2006.01) |
| *A61B 5/00* | (2006.01) |

(52) U.S. Cl.
CPC .......... *A61N 1/36025* (2013.01); *A61B 5/165* (2013.01); *A61B 5/4809* (2013.01); *A61B 5/6803* (2013.01); *A61N 1/0456* (2013.01); *A61N 1/0484* (2013.01)

(58) Field of Classification Search
CPC . A61N 1/36025; A61N 1/0456; A61N 1/0484
USPC .......................................................... 607/45
See application file for complete search history.

(56) References Cited

U.S. PATENT DOCUMENTS

| | | | | |
|---|---|---|---|---|
| 6,167,298 A | * | 12/2000 | Levin ................... | A61B 5/0482 600/545 |
| 2014/0057232 A1 | * | 2/2014 | Wetmore ............... | G09B 19/00 434/236 |
| 2014/0135886 A1 | * | 5/2014 | Cook ................... | A61N 1/0456 607/136 |

FOREIGN PATENT DOCUMENTS

WO 2012/082960 * 6/2012 ......... A61N 1/36064

OTHER PUBLICATIONS

Samuels et al. "Functional Neuroanatomy of the Noradrenergic Locus Coeruleus: Its Roles in the Regulation of Arousal and Autonomic Function Part I: Principles of Functional Organisation", Current NEuropharmacology, 2008, vol. 6, pp. 235-253.*

* cited by examiner

*Primary Examiner* — Carl H Layno
*Assistant Examiner* — Erin M Piateski

(57) ABSTRACT

A neural physiological method and apparatus for keeping the brain in wakefulness, in which the trigeminal nerves on the forehead are stimulated with a mild electrical current neuronal modulating signal of a range of frequencies and amplitudes in combination transmitted to the brain functional site locus coeruleus, resulting in inhabitation of the brain functional site thalamic reticular nucleus such that the thalamic reticular nucleus does not release inhibitory neurotransmitters for blocking the communication pathways between the thalamus and the cortical regions in the brain, keeping the brain in wakefulness.

20 Claims, 5 Drawing Sheets

NEURAL PHYSIOLOGICAL APPARATUS FOR WAKEFULNESS

RELATED APPLICATIONS

The present invention corresponds to the U.S. Provisional Patent Application 61/856,108, which has the title: "Neural Physiological Apparatus for Wakefulness".

FIELD OF THE INVENTION

The present invention is related to methods and apparatus form neural physiological modulating neuronal activation to keep the brain in wakefulness.

BACKGROUND OF THE INVENTION

For operational safety and accuracy, there is a need to keep the brain in wakefulness, for which people usually drink coffee or smoke cigarettes to keep the brain awake, and some people stimulate their head or body with mechanical or electrical means. The present invention provides a method of neural physiological stimulation to modulate neuronal activations in the brain for keeping the brain in wakefulness, including modulating upwards the neuronal activation at the brain site, locus coeruleus, via trigeminal nerve stimulation, as well as a neural physiological method of sensing the drowsiness of the brain for automatic control of the neural physiological stimulation for keeping the brain in wakefulness.

FEATURES OF THE INVENTION

The first feature of this invention is to keep the brain in wakefulness by modulating the neuronal activations of the brain drowsiness/wakefulness network including the locus coeruleus (LC), ventrolateral preoptic nucleus (VLPO), laterodorsal tegmental nucleus (LDT), pedunculopontine nucleus (PPT), thalamic reticular nucleus (TRN), via trigeminal nerve stimulation.

The second feature of this invention is to sense the brain drowsiness for automatically controlling the modulation of the neuronal activations of the brain drowsiness/wakefulness network for wakefulness.

The third feature of the present invention is to sense the brain drowsiness and to predict sleep-onset by detecting and measuring the burst of electric firing from the TRN in releasing inhibitory neurotransmitters that suppress/block communications between the thalamus and cortical regions and result in drowsiness and then further in sleep-onset.

The forth feature of the present invention is to detect and measure the bursts of electric firing from the TRN in releasing inhibitory neurotransmitters by sensing and measuring the scalp EEG features, such as the EEG spindles resulted from the burst of electric firing of the TRN in inhibitory neurotransmitter releasing.

The fifth feature of the present invention is to measure the level of drowsiness by quantifying the scalp EEG features, such as EEG spindles resulted from the burst of electric firing of the TRN in inhibitory neurotransmitter releasing, and measuring the quantities, such as the density, magnitude, and frequency of the spindles.

The sixth feature of the present invention is to predict sleep-Onset based on the quantities of the scalp EEG features resulted from the burst of electric firing of the TRN in inhibitory neurotransmitter releasing, such as the EEG spindles, including the density, magnitude, and frequency.

DESCRIPTION OF THE INVENTION

Figure 1:
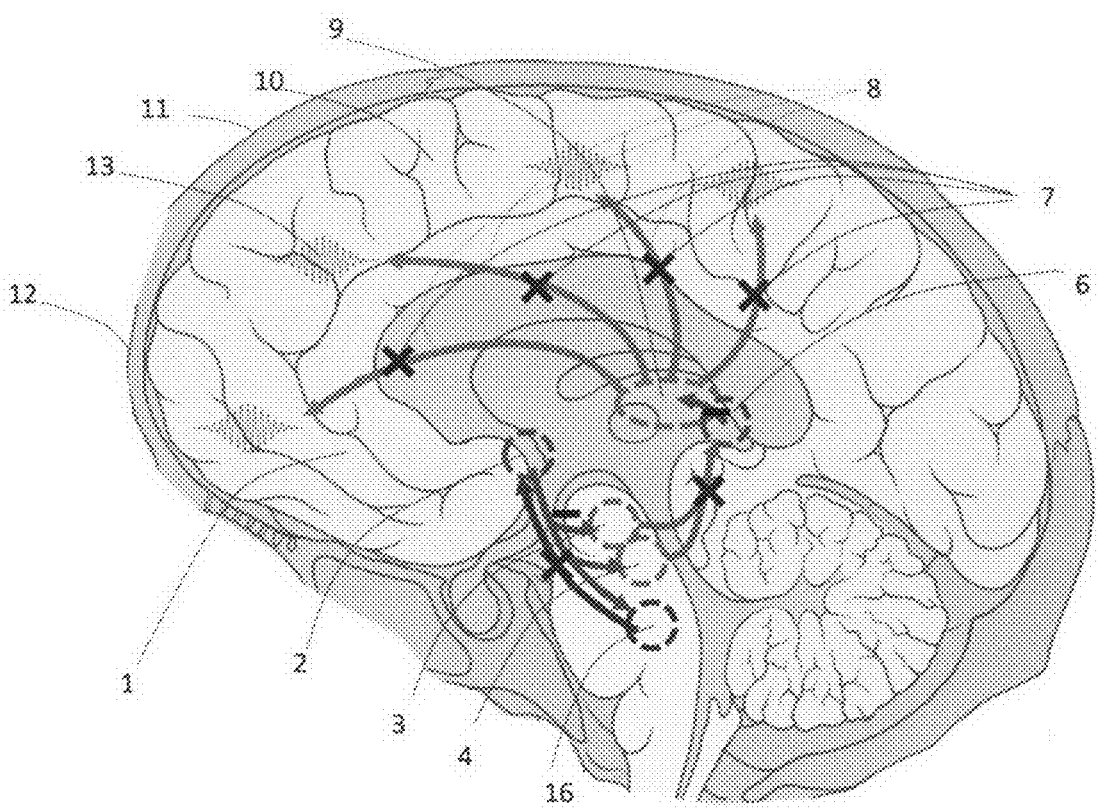
FIG. 1 shows the neurophysiologic formation mechanism of drowsiness, in which the bursts of TRN neuronal activation causes inhibitory neurotransmitter releasing in inhabitation of communication pathways between the thalamus and most cortical regions, resulting in drowsiness and then sleep-onset; and at the mean time electrically the bursts of TRN neuronal activation result in EEG spindles measureable throughout the brain and on the scalp and forehead.

As shown in FIG. 1, when the brain 1 transits from its wakefulness mode into a mode of mental fatigue/drowsiness, the sleep promoting side VLPO 2 increases in its neuronal activation, releasing inhibitory neurotransmitters to inhibit the functional sites LDT 3, PPT 4, and LC 16, and thus enabling the TRN 6 activation in bursts in releasing inhibitory neurotransmitters forming blockages 7 along the communication path ways 8 between the thalamus 9 and cortical regions 10, resulting in drowsiness mode of the brain; at the mean time of the TRN 6 activating in bursts in releasing inhibitory neurotransmitters, the neuronal activation generates neuronal electric firing bursts in special waves of electric potential throughout the brain 1, which can be measured on the scalp 11 and forehead 12 in EEG spindle waveform 13 (see FIG. 1).

Figure 2:
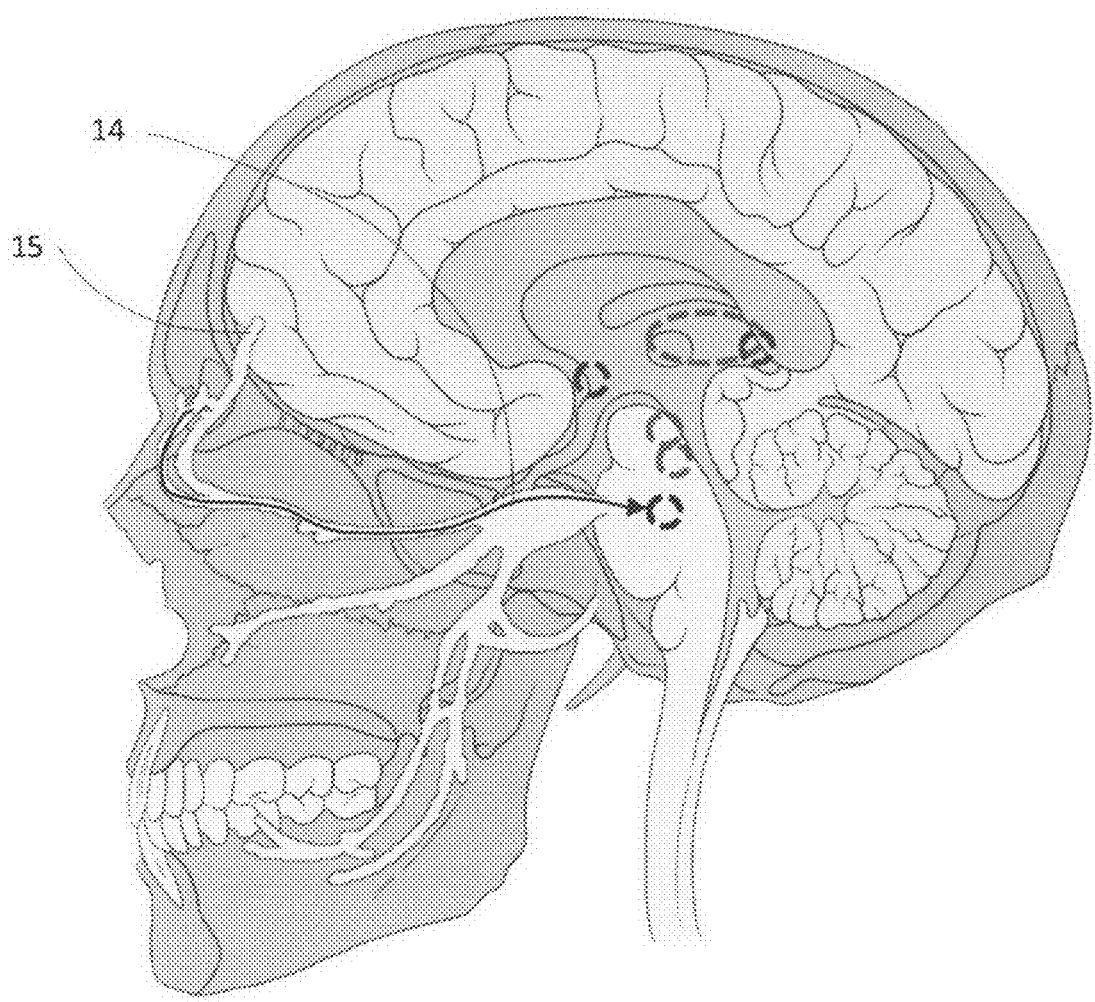
FIG. 2 shows a mild electric stimulation on the trigeminal nerve, transmitting neuronal modulating signals to the LC to modulate upwards the neuronal activation at the LC.
Figure 3:
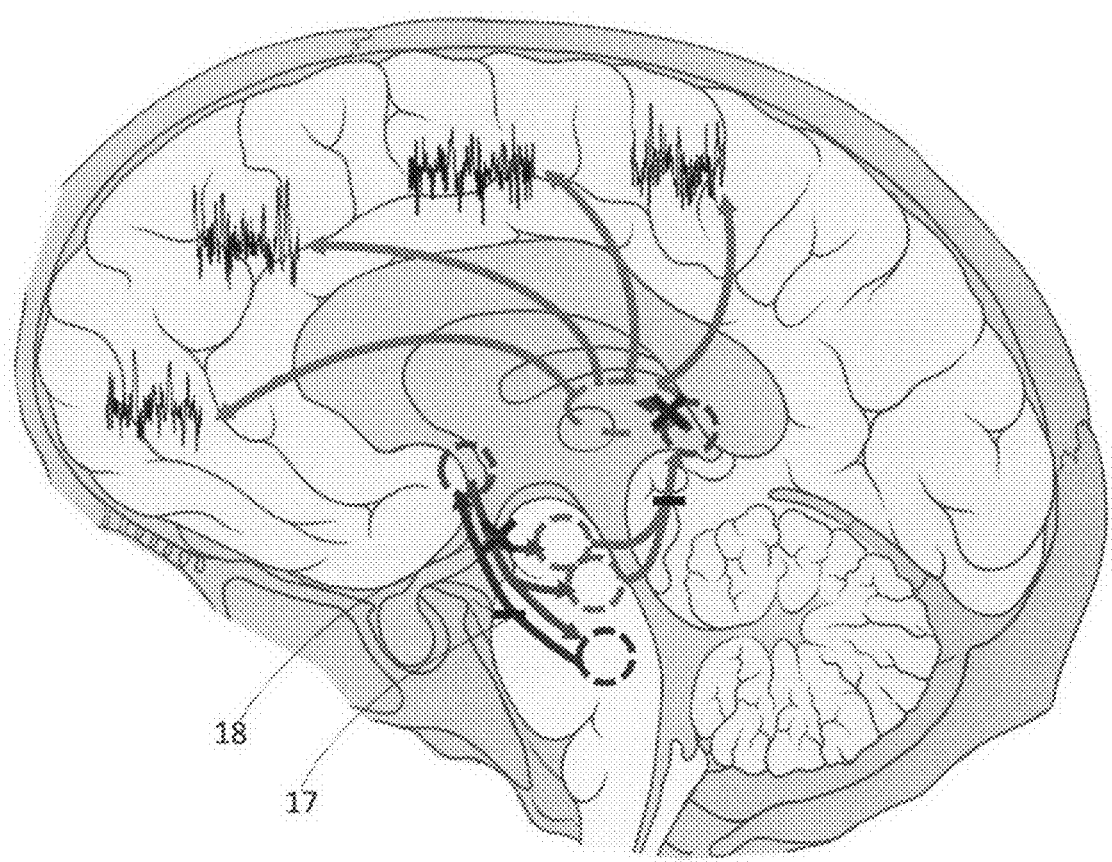
FIG. 3 shows that having the neuronal activation modulated upwards, the LC passes inhibitory transmission to the VLPO, and the inhibited VLPO losing its inhabitation on the LDT and PPT, such that LDT and PPT increase in activation and pass inhibitory transmission to the TRN, re-establishing the excitatory transmission/communications between the thalamus and cortical regions.

As shown in FIG. 2 and FIG. 3, in this invention, to keep the brain in wakefulness, the trigeminal nerves 14 on the forehead are stimulated with pulsed mild electrical current 15 of a range of frequencies and amplitudes in combination to transmit neuronal modulation signals to the brain functional site LC 16, increasing the neuronal activation at LC 16, enhancing the inhabitation pathway 17 of LC 16 to the VLPO 2, such that the VLPO 2 is inhibited, resulting a blockage 18 along its pathway in releasing inhibitory neurotransmitters to inhibit the functional sites LDT 3, PPT 4, and LC 5, and consequently the LDT 3 and PPT 4 inhibit the TRN 6 in releasing inhibitory neurotransmitters, getting the communication pathways 8 between the thalamus 9 and cortical regions 10 unblocked—keeping the brain 1 in wakefulness.

Figure 4:
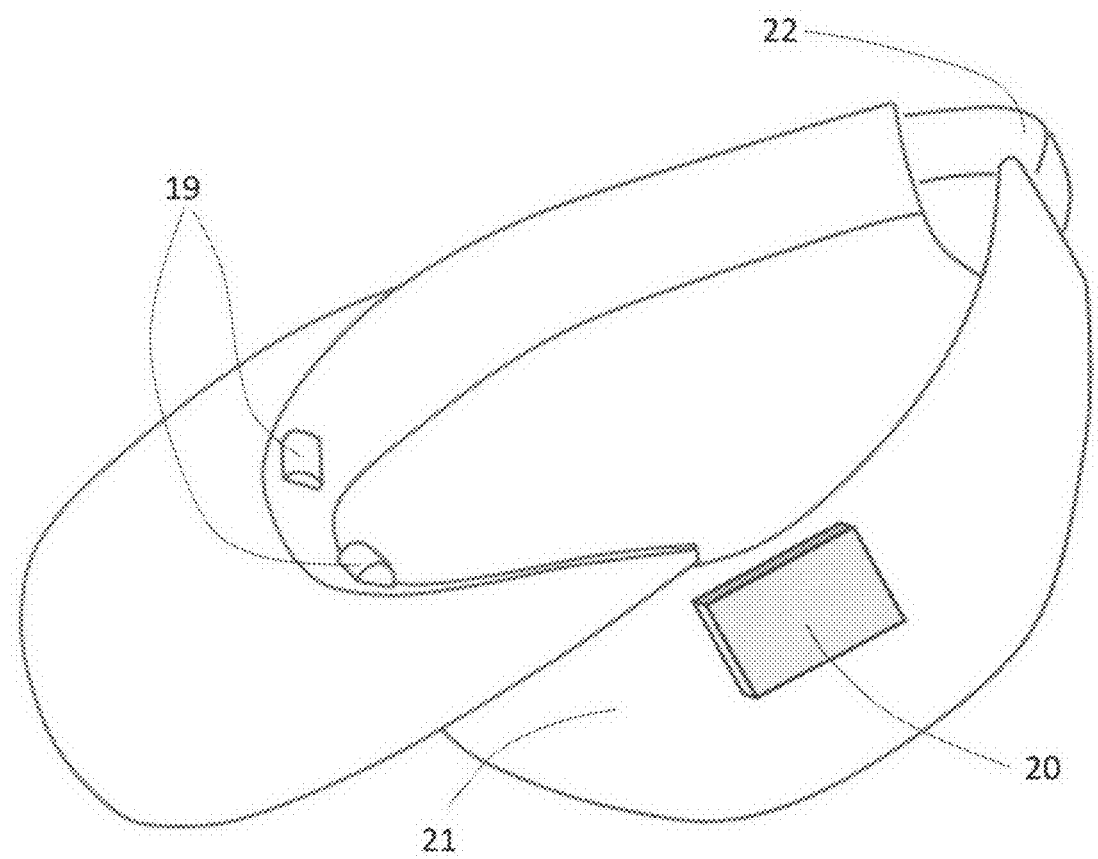
FIG. 4 shows one embodiment of the present invention, which is in a cap form with two electrodes mounted on it for contacting with the forehead, and with a battery powered circuit board mounted on it, providing one or more of the three functions: 1) the neural physiological stimulation for modulating the neuronal activation in the brain for keeping the brain in wakefulness, 2) sensing the brain drowsiness level and predicting sleep-onset based on EEG measurement, and 3) automatically turning on or off the neural physiological stimulation and automatically switching between the function modes.

Also in this invention, the triggering for turning on the trigeminal nerve stimulation to modulate up wards the LC 16 neuronal activation for keeping the brain 1 in wakefulness may be automatically controlled by detecting the EEG spindle 13 associated with brain drowsiness, through EEG measurement, such as scalp EEG measurement and signal processing, with electrodes 19 and signal processing and control circuit and battery powered board 20, as shown in FIG. 4. Once the EEG spindle 13 is detected, by the signal processing and control circuit and battery powered board 20 the trigeminal nerve stimulation 15 will be triggered on and then the neuronal activation of LC 16 will be modulated upwards, inhibiting the TRN 6 until the EEG spindle 13 disappears—keeping the brain 1 in wakefulness.

The method of the present invention may result in various embodiments of the present invention. One of the embodiments may be in a cap form, as shown in FIG. 4, in which a cap 21 for wearing on a head has two electrodes 19 on the interior front for contacting with the forehead 12 (see FIG. 1), a signal processing and control circuit and battery powered board 20, and a tightening band 22. It may provide one or more of the three functions: 1) stimulating the trigeminal nerves 14 on the forehead 12 with pulsed mild electrical current 15 of a range of frequencies and intensities in combination generated from the signal processing and control circuit and battery powered board 20, to transmit neuronal modulation signals to the brain functional site LC 16, increasing the neuronal activation at LC 16, enhancing the inhabitation pathway 17 of LC 16 to the VLPO 2, such that the VLPO 2 is inhibited, resulting a blockage 18 along its pathway in releasing inhibitory neurotransmitters to inhibit the functional sites LDT 3, PPT 4, and LC 5, and consequently the LDT 3 and PPT 4 inhibit the TRN 6 in releasing inhibitory neurotransmitters, getting the communication pathways 8 between the thalamus 9 and cortical regions 10 unblocked—keeping the brain 1 in wakefulness; 2) sensing the brain drowsiness level and predicting sleep-onset based on EEG measurement by taking EEG signals with the electrodes 19 from the forehead 12 and processing the EEG signals with the signal processing and control circuit and battery powered board 20; 3) automatically turning on or off the trigeminal nerve stimulation and automatically switch between the function modes between stimulation and sensing by the signal processing and control circuit and battery powered board 20.

Figure 5:
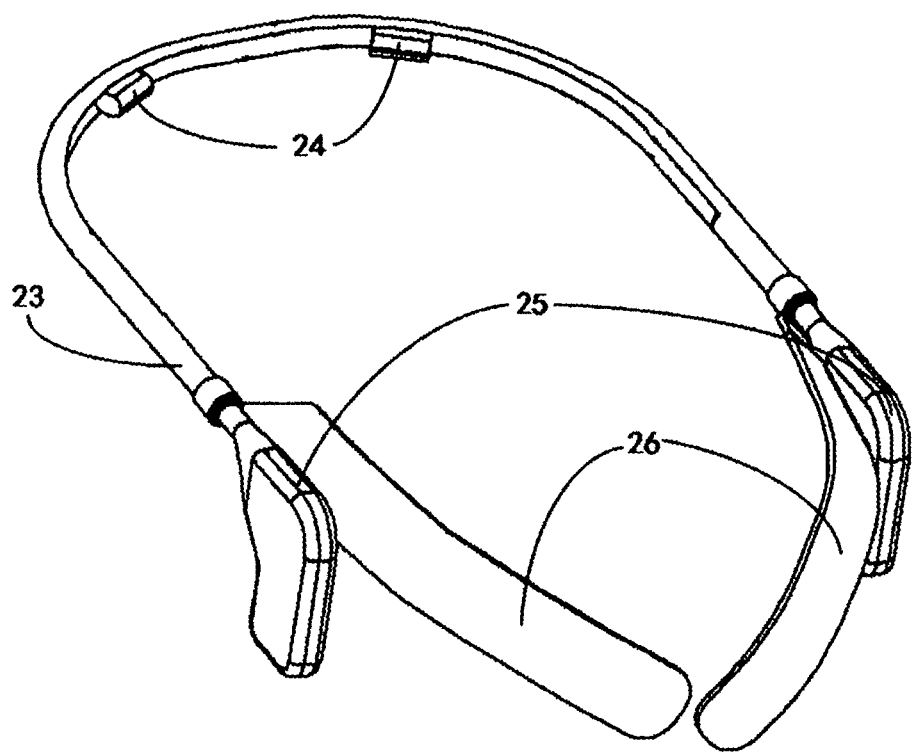
FIG. 5 shows another embodiment of the present invention, which is in a frame form with two electrodes mounted on it for contacting with the forehead, and with a battery powered circuit board on it, providing one or more of the three functions: 1) the neural physiological stimulation for modulating the neuronal activation in the brain for keeping the brain in wakefulness, 2) sensing the brain drowsiness level and predicting sleep-onset based on EEG measurement, and 3) automatically turning on or off the neural physiological stimulation and automatically switching between the function modes.

Another one of the embodiments may be in a frame form, as shown in FIG. 5, in which a frame 23 for wearing on the forehead 12 (see FIG. 1) and laying on the ears has two electrodes 24 on the interior front for contacting with the forehead 12, a pair of signal processing and control circuit and battery powered boards 25, and a tightening band 26. It may provide one or more of the three functions: 1) stimulating the trigeminal nerves 14 on the forehead 12 with pulsed mild electrical current 15 of a range of frequencies and intensities in combination generated from the signal processing and control circuit and battery powered boards 25, to transmit neuronal modulation signals to the brain functional site LC 16, increasing the neuronal activation at LC 16, enhancing the inhabitation pathway 17 of LC 16 to the VLPO 2, such that the VLPO 2 is inhibited, resulting a blockage 18 along its pathway in releasing inhibitory neurotransmitters to inhibit the functional sites LDT 3, PPT 4, and LC 5, and consequently the LDT 3 and PPT 4 inhibit the TRN 6 in releasing inhibitory neurotransmitters, getting the communication pathways 8 between the thalamus 9 and cortical regions 10 unblocked—keeping the brain 1 in wakefulness; 2) sensing the brain drowsiness level and predicting sleep-onset based on EEG measurement by taking EEG signals with the electrodes 24 from the forehead 12 and processing the EEG signals with the signal processing and control circuit and battery powered boards 25; 3) automatically turning on or off the trigeminal nerve stimulation and automatically switch between the function modes between stimulation and sensing by the signal processing and control circuit and battery powered boards 25.

The invention claimed is:

1. A neural physiological method for keeping a brain in wakefulness, comprising:
neural physiologically stimulating, by an electronic system, at EEG sleep spindle frequency nerves on a body or head to pass neuromodulation signals of EEG sleep spindle frequency to a brain functional site LC,
modulating its firing rate upwards to inhibit a brain functional site VLPO such that a brain functional site TRN is inhibited and to keep the brain in wakefulness; and
automatically triggering a neural physiological stimulation to be turned on and turned off by sensing a brain drowsiness level and predicting sleep-onset based on EEG measurement,
wherein the electronic system comprises one or more electrodes placed on the head, including forehead, faces, and/or other parts of the head, and
wherein said EEG measurement includes measuring EEG sleep spindle frequency, and/or density, and/or magnitude.

2. The neural physiological method of claim 1, wherein said nerves are trigeminal nerves on the head, said stimulation is electromagnetic stimulation, said neuromodulation signals are electrical pulses of a range of frequencies in combinations generated by the electronic system.

3. The neural physiological method of claim 1, wherein said modulating upwards the firing rate of the brain functional site LC is configured to be achieved by trigeminal nerve stimulation.

4. The neural physiological method of claim 3, wherein the trigeminal nerve stimulation is configured to be achieved by placing two or more electrodes toward part of the trigeminal nerves and passing modulating signals via electric current passing through the trigeminal nerves.

5. The neural physiological method of claim 4, wherein said electrodes are dry or wet electrodes.

6. The neural physiological method of claim 4, wherein said electric current is configured to be provided by a battery powered electric circuit.

7. The neural physiological method of claim 1, wherein said EEG measurement includes measurement of the bursts of the TRN neuronal activation in releasing inhibitory neurotransmitters that block communications between thalamus and cortical regions and result firstly in mental-fatigue/drowsiness and further in sleep-onset.

8. The neural physiological method of claim 7, wherein said mental-fatigue/drowsiness is configured to be measured by sensing the bursts of TRN neuronal activation.

9. The neural physiological method of claim 8, wherein said sensing of the bursts of TRN neuronal activation is configured to be by any scalp EEG measurement.

10. The neural physiological method of claim 9, wherein said scalp EEG measurement is in a setup with one or more electrodes placed on the head, an analog signal amplifier, a digital signal processor with or without data storage and display, with or without wireless transmission.

11. The neural physiological method of claim 10, wherein said locations of the EEG electrode placement is on any part of the head or body, including the forehead and/or along the center line of the head from front to back.

12. The neural physiological method of claim 10, wherein said EEG electrodes are the conventional electrolyte gel types EEG electrodes, any types of dry EEG electrodes/sensors, and/or any types of active EEG electrodes/sensors that contain electric circuits.

13. The neural physiological method of claim 10, wherein said analog signal amplifier is an EEG amplifier or an analog signal amplifying circuit.

14. The neural physiological method of claim 10, wherein said digital signal processor is configured to be formed by one or more digital signal processing chip(s) or a computer.

15. The neural physiological method of claim 8, wherein said measurement of the bursts of TRN electric firing includes sensing features, characteristics, or any indications of the bursts in any ways.

16. The neural physiological method of claim 15, wherein said features, characteristics, or any indications of the bursts include EEG sleep spindles and any EEG sleep waves.

17. The neural physiological method of claim 1, wherein said sleep-onset prediction based on measurement of the bursts of TRN neuronal activation includes predicting sleep-onset from the measured EEG sleep spindle frequency, and/or density, and/or magnitude.

18. A neural physiological apparatus, configured to implement the method according to claim 1.

19. The neural physiological apparatus according to claim 18, wherein said apparatus is in a cap form with two electrodes mounted on it for contacting with the forehead, and with a battery powered circuit board mounted on it, providing one or more of three functions: 1) said neural physiological stimulation for modulating neuronal activation in the brain for keeping the brain in wakefulness, 2) said sensing the brain drowsiness level and predicting sleep-onset based on EEG measurement, and 3) said automatically turning on or off the neural physiological stimulation and automatically switching between function modes.

20. The neural physiological apparatus according to claim 18, wherein said apparatus is in a frame form with two electrodes mounted on it for contacting with the forehead, and with a battery powered circuit board on it, providing one or more of three functions: 1) said neural physiological stimulation for modulating neuronal activation in the brain for keeping the brain in wakefulness, 2) said sensing the brain drowsiness level and predicting sleep-onset based on EEG measurement, and 3) said automatically turning on or off the neural physiological stimulation and automatically switching between function modes.

* * * * *